United States Patent [19]

Anderson et al.

[11] Patent Number: 5,892,123

[45] Date of Patent: Apr. 6, 1999

[54] PROCESS FOR REPRODUCING A MIXTURE CONTAINING CYCLODODECANONE AND CYCLODODECANOL

[75] Inventors: Howard Wayne Anderson, Hockessin; James Bernard Sieja, Newark, both of Del.

[73] Assignee: E. I. du Pont de Nemours and Company, Wilmington, Del.

[21] Appl. No.: 17,784

[22] Filed: Feb. 3, 1998

[51] Int. Cl.$^6$ .............................. C07C 45/53; C07C 35/08
[52] U.S. Cl. ..................... 568/361; 568/342; 568/344; 568/821
[58] Field of Search ....................... 568/342, 835, 568/798, 385, 578, 361, 821, 375, 832, 344

[56] References Cited

U.S. PATENT DOCUMENTS

| 4,465,861 | 8/1984 | Hermollin | 568/342 |
| 4,568,769 | 2/1986 | Yashima | 568/342 |

FOREIGN PATENT DOCUMENTS 1032390  6/1966  United Kingdom .

*Primary Examiner*—Shailendra Kumar
*Assistant Examiner*—Sreeni Padmanabhan

[57] ABSTRACT

A method is disclosed for catalytically decomposing cyclododecyl hydroperoxide into cyclododecanone and cyclododecanol using a chromium catalyst.

7 Claims, No Drawings

PROCESS FOR REPRODUCING A MIXTURE CONTAINING CYCLODODECANONE AND CYCLODODECANOL

BACKGROUND OF THE INVENTION

Cyclododecanone (K) and cyclododecanol (A) are intermediates in the production of nylon-12 and 1,12-dodecanedioic acid (DDDA). The air oxidation of cyclododecane produces a mixture containing K, A and a significant amount of cyclododecyl hydroperoxide (P). The P can be decomposed into more K and A. A boron compound may be used as a catalyst for the decomposition; see UK Patent No. 1,032,390.

U.S. Pat. No. 4,465,861 discloses a process for the conversion of cyclohexyl hydroperoxide to a mixture of cyclohexanone and cyclohexanol using, among others, a salt of chromium, such as chromium octoate, and a stabilizing agent. Cyclohexyl hydroperoxide can be made from the oxidation of cyclohexane. The oxidation results in a reaction mixture containing cyclohexanone, cyclohexanol, cyclohexyl hydroperoxide, unreacted cyclohexane, as well as some water and acids. Before the cyclohexyl hydroperoxide in this reaction mixture can be decomposed with a chromium catalyst to provide more cyclohexanone and cyclohexanol, the acids must be washed away with water, and substantially all the water—both that produced during cyclohexanone oxidation and that used to wash away the acids—must be removed. Typical cyclohexanone and cyclohexanol production from peroxide decomposition results in cyclohexanone to cyclohexanol ratios of about 3.

Because it is expensive to dispose of boron-containing waste from commercial operations, there is a need for a process for the conversion of cyclododecane to DDDA that does not use a boron compound to facilitate the decomposition of cyclododecyl hydroperoxide. There is also a need to decompose cyclododecyl hydroperoxide in a manner that results in a high ratio of K to A. Cyclododecanone (K) is a more valuable product than cyclododecanol (A): cyclododecanone can be converted to the corresponding lactam and ultimately to nylon-12, and cyclododecanone can also be used cost-efficiently to produce DDDA, since it is already partially oxidized from A. Finally, there is a need to be able to catalytically decompose cyclododecyl hydroperoxide without the need to wash away acids formed during cyclododecane oxidation and without the need to remove water.

SUMMARY OF THE INVENTION

These needs are met by the present invention which is a process for producing a mixture containing cyclododecanone and cyclododecanol, comprising oxidizing cyclododecane to provide a reaction mixture containing cyclododecyl hydroperoxide and contacting the reaction mixture with a chromium catalyst.

It has been found that when a chromium catalyst is used in accordance with the present invention, there is a surprising increase in the ratio of K to A, based on ratios typically obtained from cyclohexyl hydroperoxide decomposition. It also has been found that, unlike cyclohexane oxidation product, cyclododecane oxidation product may be treated with a chromium catalyst without the need to wash the oxidation product with water, and without the need to remove the water.

DETAILED DESCRIPTION

In accordance with the present invention, the cyclododecyl hydroperoxide (P), resulting from the oxidation of cyclododecane, is decomposed to cyclododecanone (K) and cyclododecanol (A) in the presence of a chromium catalyst.

Cyclododecyl hydroperoxide may be obtained by oxidation of cyclododecane. Air oxidation is the preferred method. This may be performed by bubbling air through cyclododecane at a temperature of about 145° C. to about 180° C. Normally conversion is about 10%. The resulting oxidation product is a solution which contains unreacted cyclododecane, cyclododecyl hydroperoxide, cyclododecanone, cyclododecanol, and other impurities.

The resulting oxidation product solution is then treated with a chromium catalyst to decompose the cyclododecyl hydroperoxide to cyclododecanone and cyclododecanol. This chromium-catalyzed process gives a product which is rich in cyclododecanone (K) relative to cyclododecanol (A). Although ratios of K to A as high as 25 have been observed, typical K to A ratios are 5 to 10.

The chromium catalyst may be any chromium salt soluble in cyclododecane, a non-polar medium. Examples of such homogeneous (i.e., soluble) catalysts include chromium octoate, chromium naphthenate, chromium laurate, and chromium ethylhexanoate. Chromium salts of fatty acids which are soluble in hydrocarbon solvents are particularly preferred. The catalyst may also be heterogeneous (i.e., insoluble). The chromium may be contained on an ion exchange resin. Examples of these include sulfonic acid resins such as Amberlist 15, Amberlist XN-100, Dowex M-31, and Dowex DR-2030. Amberlist is a trademark of Rhom and Haas. Dowex is a trademark of Dow.

Typically the homogeneous chromium catalyst is present in a concentration of 0.5 to 10 ppm, most preferably 1 to 4 ppm. based on the total reaction mixture.

Pressure is not an important factor. Typically, the cyclododecyl hydroperoxide decomposition is conducted at atmospheric pressure for ease and cost of operation. Typical reaction temperatures are 80° to 165° C., preferably 100° to 120° C.

Optionally, the decomposition portion of the process of the present invention can be run in the presence of air which results in high K/A ratios and conversion of some unreacted cyclododecane to K and A.

The present process does not require that the cyclododecane oxidation product be washed with water to remove acids or that water be removed from the oxidation product before addition of the chromium catalyst.

EXAMPLES

The following nonlimiting examples illustrate the present invention.

Example 1

This example shows the need to wash cyclohexane oxidate (but not cyclododecane oxidate) prior to hydroperoxide decomposition by a chromium catalyst.

The reactor consisted of a 50 ml round-bottomed flask equipped with a condenser topped with a nitrogen tee, Teflon® stirring bar, thermocouple, and a Teflon®-coated rubber septum for catalyst injection and sample removal. The flask was charged with 12 grams of oxidate containing about 0.12 grams of an internal standard (tetradecane for cyclohexane oxidate, hexacosane for cyclododecane oxidate), and brought to temperature. A zero time sample was removed when the solution reached the desired temperature (79° C.), and was analyzed, after silylation, by gas chromatography using a Hewlett Packard HP 50 capillary column. 50 microliters of chromium octoate solution in toluene were added so that the final concentration of Cr in the solution was 5 ppm. About 0.2 ml samples were removed at various times and analyzed. The wt % K, A, P were determined. The increase in K divided by the increase in A is termed delta K/delta A in the Table 1.

The oxidates were obtained from commercial facilities. The C6 (cyclohexane) washing procedure involved washing the C6 oxidate twice with 5% water for 30 min at 72° C. The resulting phases were separated and the organic phase was dried with magnesium sulfate.

It is clear from Table 1, that for chromium to be an effective cyclohexyl hydroperoxide decomposition catalyst, the cyclohexane oxidate must be washed with water. It is also clear that C12 (cyclododecane) oxidate does not require water washing to obtain hydroperoxide conversions similar to those obtained from washed C6 oxidate. It is also clear that the delta K/delta A ratio obtained from C12 oxidate is higher than that from C6 oxidate.

TABLE 1

| TIME (MIN) | % K | % A Wt % | % P | % P conv | delta K / delta A | Oxidate identity/ treatment |
|---|---|---|---|---|---|---|
| 0 | 1.86 | 3.64 | 0.57 | 0 |  | C6/none |
| 30 | 1.95 | 3.82 | 0.65 | 0 |  |  |
| 60 | 1.98 | 3.86 | 0.59 | 0 |  |  |
| 90 | 1.98 | 3.81 | 0.67 | 0 |  |  |
| 0 | 2.0 | 3.81 | 0.63 | 0 |  |  |
| 30 | 2.4 | 4.1 | 0.29 | 54 | 1.38 | C6/washed |
| 60 | 2.48 | 4.27 | 0.086 | 86 | 1.04 |  |
| 90 | 2.53 | 4.33 | 0.058 | 91 | 1.0 |  |
| 0 | 0.5 | 0.12 | 0.59 |  |  | C12/none |
| 30 | 0.91 | 0.17 | 0.17 | 72 | 8.7 |  |
| 60 | 0.95 | 0.18 | 0.13 | 78 | 7.5 |  |
| 90 | 0.97 | 0.18 | 0.12 | 80 | 7.8 |  |
| 0 | 1.05 | 0.51 | 2.73 |  |  | C12/none |
| 30 | 2.84 | 0.64 | 0.58 | 79 | 14.6 |  |
| 60 | 3.0 | 0.66 | 0.4 | 85 | 14.3 |  |
| 90 | 3.1 | 0.67 | 0.37 | 87 | 13 |  |

Example 2

This example shows the effect of air on the delta K/delta A ratio for a cyclododecane oxidate.

The reactor consisted of a cylindrical glass tube about 2 cm in diameter by 11 cm long, containing a concentric inner tube about 2 mm in diameter, which terminated in a 1 cm fritted tip near the bottom of the larger tube. It was charged with about 3 grams of C12 (cyclododecane) oxidate containing about 0.3 grams of internal standard. The tube was immersed in an oil bath at the desired temperature. On melting, nitrogen was blown through the melt at a rate of 25 cc/min, which provided agitation. When the melt reached the desired temperature (90° C.), a sample was taken at time zero, and a solution of chromium octoate in toluene was injected into the melt so that the resulting concentration of Cr in the final solution was 5 ppm. About 0.2 ml samples were removed at various times and analyzed by GC on a Hewlett Packard HP 50 capillary column after silylation. The wt % K, A, P were determined.

To determine the effect of air on the results, when the melt reached the desired temperature and a zero time sample was taken, the nitrogen purge was replaced with an air purge. The effect of the air is shown in Table 2, where it is shown that the delta K/delta A ratio increased to 30–35 from 9–12. Since K is the more valuable product (for example, for nylon-12 manufacture) the present invention is an economically attractive method for obtaining oxidate rich in K.

TABLE 2

| TIME (MIN) | % K | % A Wt % | % P | % P conv | delta K / delta A | Oxidate identity/ treatment |
|---|---|---|---|---|---|---|
| 0 | 0.94 | 0.79 | 5.4 |  |  | nitrogen |
| 15 | 5.0 | 1.1 | 0.8 | 85 | 12 |  |
| 30 | 5.3 | 1.2 | 0.4 | 92 | 9.6 |  |
| 60 | 5.3 | 1.3 | 0.3 | 94 | 9.3 |  |
| 0 | 1.1 | 0.8 | 5.5 |  |  | air |
| 15 | 5.6 | 0.92 | 0.7 | 87 | 31 |  |
| 30 | 6.1 | 0.9 | 0.3 | 95 | 30 |  |
| 60 | 6.3 | 0.92 | 0.2 | 97 | 35 |  |

What is claimed is:

1. A process for producing a mixture containing cyclododecanone (K) and cyclododecanol (A), comprising oxidizing cyclododecane to provide an oxidation product containing cyclododecylhydroperoxide and an initial amount of K ($K_i$) and an initial amount of A ($A_i$) and contacting the oxidation product with a chromium catalyst to provide a mixture containing a final amount of K ($K_f$) and a final amount of A ($A_f$) in which ($K_f$-$K_i$)/($A_f$-$A_i$) is greater than about 5.

2. The process of claim 1 in which the chromium catalyst is chromium octoate.

3. The process of claim 1 in which the oxidation product is contacted with the chromium catalyst in the presence of water.

4. The process of claim 1 in which the oxidation product is contacted with the chromium catalyst in the presence of air or nitrogen.

5. The process of claim 4 in which the oxidation product is contacted with the chromium catalyst in the presence of air.

6. The process of claim 3 in which the oxidation product is contacted with the chromium catalyst in the further presence of air or nitrogen.

7. The process of claim 6 in which the oxidation product is contacted with the chromium catalyst in the presence of air.

* * * * *